US007984710B2

(12) United States Patent
Von Schuckmann

(10) Patent No.: US 7,984,710 B2
(45) Date of Patent: Jul. 26, 2011

(54) INHALER DEVICE

(76) Inventor: Alfred Von Schuckmann, Kevelaer (DE)

( * ) Notice: Subject to any disclaimer, the term of this patent is extended or adjusted under 35 U.S.C. 154(b) by 261 days.

(21) Appl. No.: 12/254,106

(22) Filed: Oct. 20, 2008

(65) Prior Publication Data

US 2009/0038611 A1 Feb. 12, 2009

Related U.S. Application Data

(60) Division of application No. 11/747,051, filed on May 10, 2007, which is a continuation of application No. PCT/EP2005/054138, filed on Aug. 23, 2005.

(30) Foreign Application Priority Data

Nov. 10, 2004 (DE) .......................... 10 2004 054 179
Jul. 18, 2005 (DE) .......................... 10 2005 033 398

(51) Int. Cl.
*A61M 11/00* (2006.01)
*A62B 7/00* (2006.01)
*A62B 9/00* (2006.01)

(52) U.S. Cl. .......... 128/200.23; 128/200.14; 128/205.23

(58) Field of Classification Search ............. 128/200.23, 128/203.12, 203.15, 205.23, 203.19, 203.21; 222/32, 36, 38; 116/311, 312, 307, 317, 116/318

See application file for complete search history.

(56) References Cited

U.S. PATENT DOCUMENTS

| 5,228,586 | A | 7/1993 | Fuchs |
| 5,971,140 | A | 10/1999 | Frutin |
| 6,076,521 | A * | 6/2000 | Lindahl et al. ........... 128/203.15 |
| 6,283,365 | B1 * | 9/2001 | Bason ............................ 235/116 |
| 6,431,168 | B1 | 8/2002 | Rand et al. |
| 6,446,627 | B1 | 9/2002 | Bowman et al. |
| 7,156,258 | B2 * | 1/2007 | Eckert .............................. 222/23 |
| 7,464,708 | B2 * | 12/2008 | Marx ........................ 128/205.23 |
| 2004/0144798 | A1 | 7/2004 | Ouyang et al. |
| 2004/0149772 | A1 * | 8/2004 | Ouyang ........................... 222/36 |
| 2004/0211420 | A1 | 10/2004 | Minshull et al. |

FOREIGN PATENT DOCUMENTS

| EP | 0 480 488 A1 | 5/1991 |
| EP | 1 065 477 A2 | 3/2000 |
| WO | 0128887 A1 | 4/2001 |
| WO | 2004071563 A1 | 8/2004 |

OTHER PUBLICATIONS

International Search Report, Mar. 7, 2006, 8 pages.

\* cited by examiner

*Primary Examiner* — Justine R Yu
*Assistant Examiner* — Valerie Skorupa
(74) *Attorney, Agent, or Firm* — St. Onge Steward Johnston & Reens LLC

(57) ABSTRACT

A hand-held device for apportioned delivery of sprayable substances, in particular inhaler medicaments, having a cartridge which is displaceable by pressing in a housing into the open position for delivery, and an indexing mechanism which is moved along by the cartridge during the opening stroke of the cartridge for registering and displaying delivery actuations which have been carried out, which indexing mechanism is disposed in a housing centrally below the opening-side end wall of the cartridge, overlappingly with respect to the valve tube of the cartridge. In order to configure a hand-held device of the type in question in a spatially advantageous manner with a simplified construction and such that it is more reliable in terms of handling, it is proposed to displace plate-shaped housing as a whole with the cartridge, except for a step-by-step indexing finger star disposed therein.

7 Claims, 6 Drawing Sheets

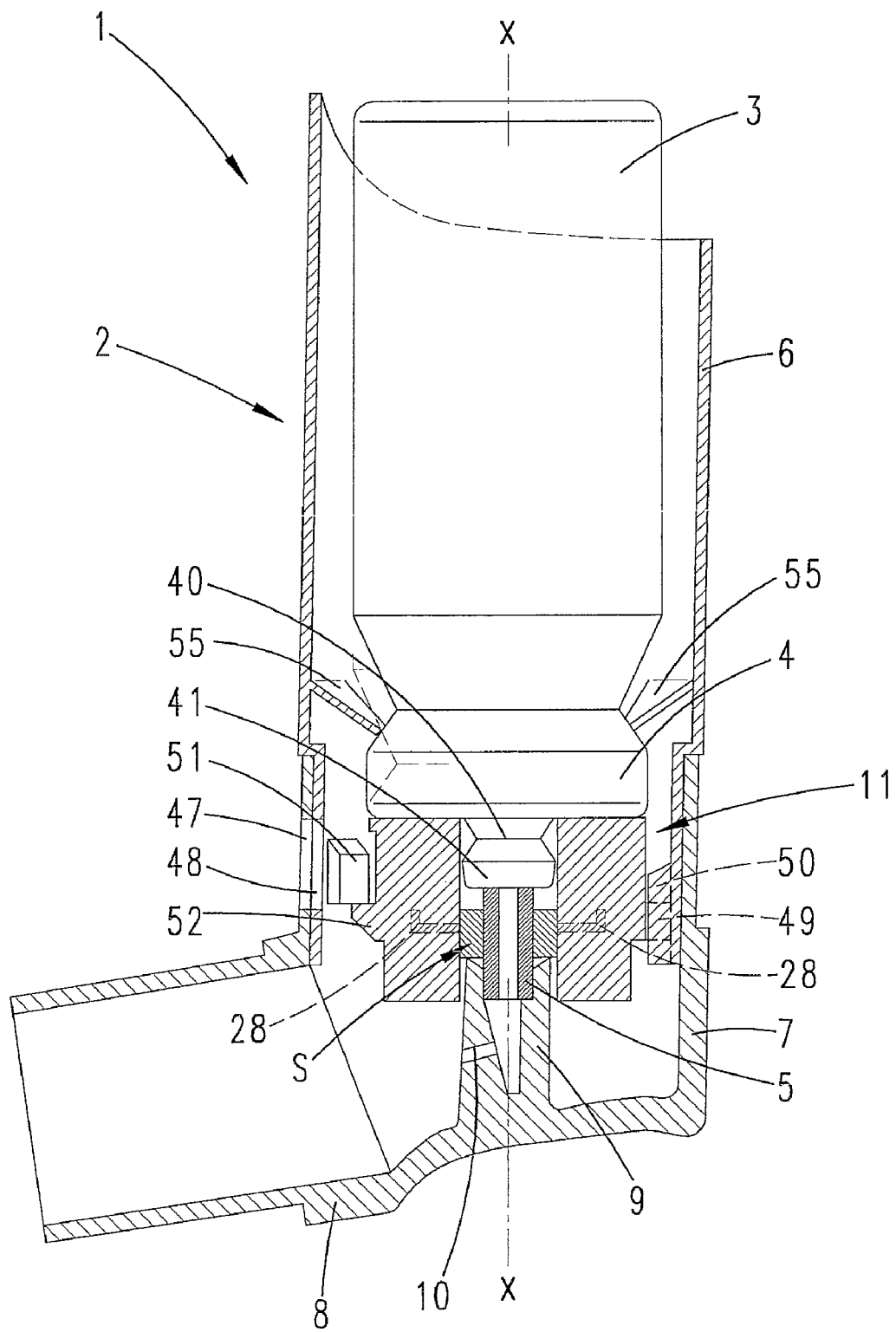

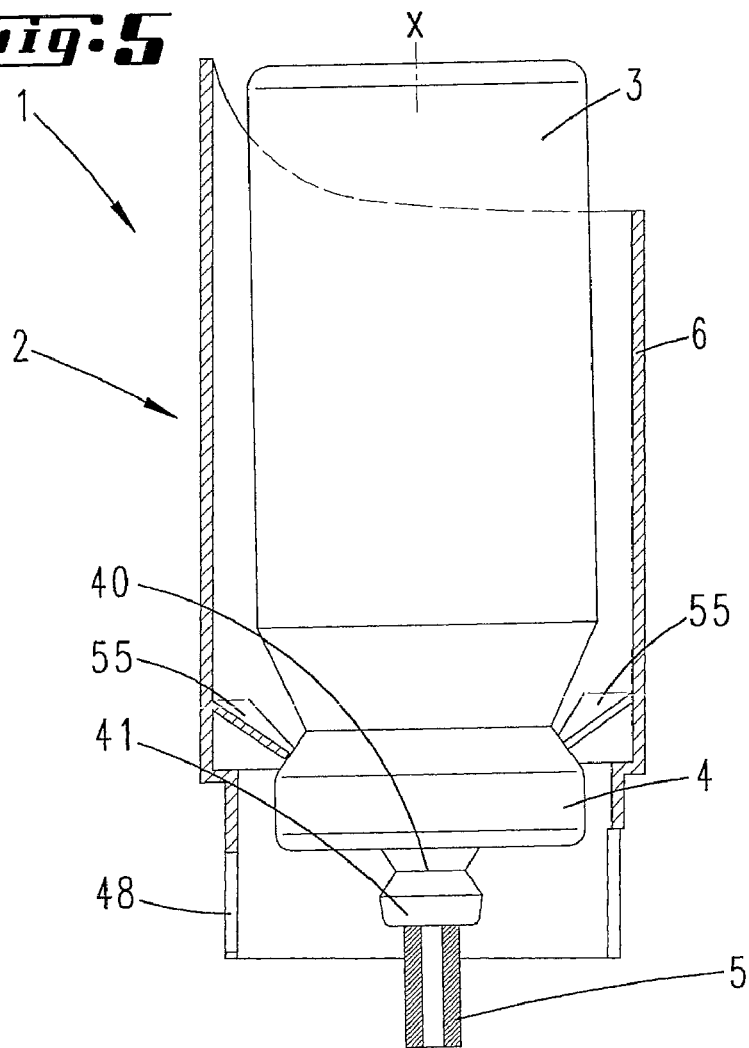
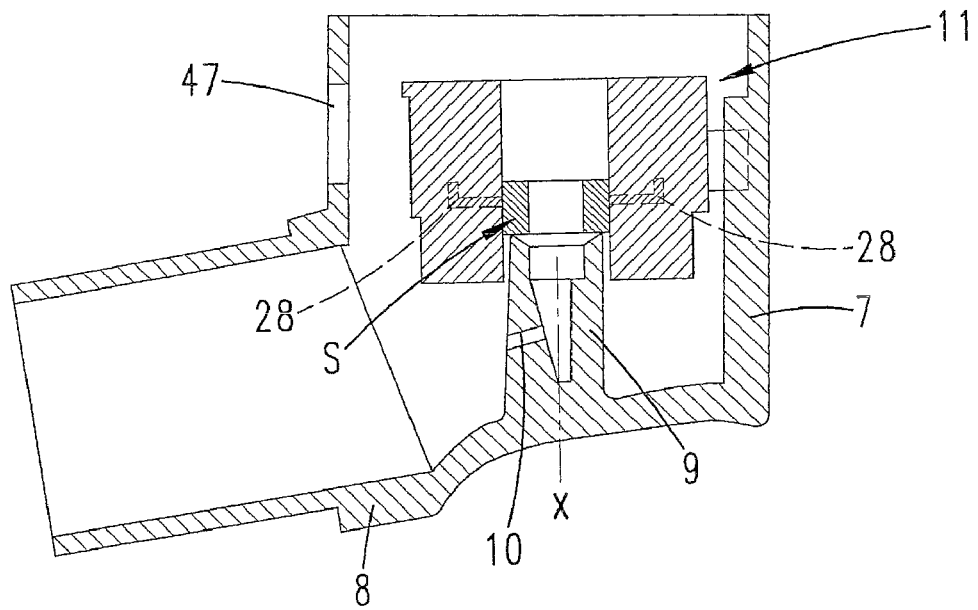
Fig. 5

INHALER DEVICE

CROSS-REFERENCE TO RELATED APPLICATIONS

The present application is a division of pending U.S. patent application Ser. No. 11/747,051, filed May 10, 2007, which in turn is a continuation of International patent application PCT/EP2005/054138 filed on Aug. 23, 2005 which designates the United States and claims priority from German patent applications Nos. 10 2004 054 179.5 filed on Nov. 10, 2004 and 10 2005 033 398.2 filed on Jul. 18, 2005. All prior applications are herein incorporated by reference.

FIELD OF THE INVENTION

The invention relates to a hand-held device according to the preamble of the main claim.

BACKGROUND OF THE INVENTION

Hand-held devices of the type in question are used in particular in medicinal aerosol therapy for the treatment of respiratory complaints. The pressurized cartridge mounted in the housing of the hand-held device contains the medicament to be inhaled, with, in order to release or to eject the same, an axial displacement of the cartridge in the housing of the hand-held device being required. For this purpose, the cartridge is equipped with a valve for discharging a predetermined quantity of medicament. The housing of the hand-held device, which generally virtually completely surrounds the cartridge, furthermore has in conventional manner a mouthpiece and/or an adapter for inhalation through the nose. It is necessary to provide the user with a counting device which displays the consumed quantity of medicament or the quantity of medicament still present in the cartridge. Since a defined quantity of medicament is discharged upon each actuation of the cartridge, it is known to couple the counting device to the axial displacement of the cartridge in the inhaler housing for delivery of medicament. For each opening stroke of the cartridge, an annular scale is rotated. If the scale disk turns about an axis which is perpendicular to the stroke of the cartridge (U.S. Pat. No. 6,431,168), the lateral surface that carries the numerical values and faces the viewing window may be only very small, on account of the only limited space underneath the cartridge. The solution also already known is therefore more advantageous, to provide a scale ring which turns about an axis that coincides with the axis of the cartridge (US 2004/0144798). The plane of rotation of the scale ring is then fixed and is in front of a viewing window of the housing of the hand-held device.

It is an object of the invention to improve a solution of this kind, in particular in respect of its technical usage.

SUMMARY OF THE INVENTION

This problem is solved by the invention specified in the main claim.

As a result of this configuration, the user, for example on first use or after an extended period of non-use of the inhaler, can check, by gentle pressure on the cartridge, if the main elements are in order. The invention makes use of the standard that applies to all of these cartridges, that all of these cartridges only open, i.e. dispense a dose, when a full stroke has been completed. The travel executed according to the invention by the scale ring behind the viewing window is easy to recognize; a partial rotation of the scale ring would not be, the more so since for reasons of space on the lateral surface of the scale ring, it is not possible to apply too many scale markings, even though a numerical indication is to come up at specific spacings and/or also even though a step-down drive is to be inserted into the scale ring rotation. Advantageously, the viewing window is located on the side of the holding housing on which the mouthpiece is also present.

A step-action indexing mechanism is provided, which on account of the arrangement selected for the various indexing members, may have an advantageous and space-saving construction. Further space-saving optimization is also achieved by the clearance present beneath the cartridge in the housing of the hand-held device being functionally incorporated into the operating control.

The subject matters of the rest of the claims are explained below in relation to the subject matter of claim 1, but may also be important in their independent formulation.

Thus it is further provided that the step-action indexing mechanism has a rotary ring that is concentric with the valve tube and has an external scale, the scale being rotated in a stepwise manner via a planet-gear drive by a rotary toothed rim which is likewise concentric with the valve tube and is driven by an opening stroke of the cartridge. In the event of possible removal of the step-action indexing mechanism from the housing of the hand-held device—e.g. for cleaning purposes—the absence then of the supporting portion for the indexing finger means that an inadvertent, cartridge-independent actuation of the step-action indexing mechanism is not possible. The planet-gear mechanism preferably passes on the angle of rotation to the scale ring in stepped-down form. For example, 200 or 300 stroke actions can accordingly be shown on the scale ring to match the volume of the cartridge. It is further preferred for the graduated scale of the scale ring, which is disposed on the outer lateral surface of the scale ring and extends in front of a viewing window of the housing, to correspond in each case to a number of individual rotary steps of the planet gear. In this respect, it proves to be advantageous, furthermore, for, as far as the step-down transmission is concerned, an individual rotary step of the planet gear to take place following completion of a number of individual rotary steps of the sun gear. The planet gear, furthermore, is in engagement, in the radially outward direction, with a toothed rim. The latter has at least one slot which extends, directed obliquely upwards, from the lower peripheral edge, for entry of the step-action indexing finger, in order to predetermine thereby the indexing direction of the finger for rotating the disk on the sun gear further in a stepwise manner. The housing for the step-action indexing mechanism with the further indexing components is displaced relative to the step-action indexing finger star, this with movement of the step-action indexing finger in the plane oriented perpendicular to the longitudinal axis which effects the further step-action of the counting mechanism. The gone down scale is a kind of element for indicating that functioning is taking place correctly. After the cartridge is released, it moves back quickly into its basic position on account of the integrated valve spring, this effecting a speedy return action of the step-action indexing mechanism, there being no longer any bias by the housing of the step-action indexing mechanism. This is achieved by the prestressed step-action indexing finger, which automatically assumes again its original position, directed obliquely upwardly, and thereby urges the indexing members as well as the housing of the step-action indexing mechanism into their original position. Accordingly, the step-action indexing mechanism is uncoupled from the cartridge in respect of the return movement into its basic position, but it is controllable by the turning scale. It is controlled by a return spring formed by the step-action indexing finger. The axial length of the entire step-action indexing mechanism is furthermore preferably matched to the length of extent of the valve tube; accordingly, the latter furthermore remains surrounded in a protected position by the housing of the step-action indexing mechanism in the position in which it has been removed from the housing of the hand-held device. As an alternative, the housing of the step-action indexing mechanism, the housing being configured as a flat plate, may be latched in the housing in such a manner that it can still be displaced inwards by the opening stroke. Thus, for example during a first assembly of the hand-held device, the step-action indexing mechanism can be pushed, together with the cartridge, into the housing of the hand-held device, whereupon the housing of the step-action indexing mechanism finally engages behind a catch provided in the housing. The step-action indexing mechanism can furthermore be displaced inwards from this basic position via the stroke movement of the cartridge. In a development of the subject matter of the invention, a double latching of the housing of the step-action indexing mechanism, the housing being configured as a flat plate, is provided in such a manner that, in addition to the latching to the collar of the cartridge, a second stronger latching takes place in the housing of the hand-held device. Before using for the first time, it is necessary to fit the housing of the hand-held device to the cartridge.

BRIEF DESCRIPTION OF THE DRAWINGS

The invention is explained in more detail hereinbelow with reference to the accompanying drawing, which merely illustrates various exemplary embodiments and in which:

FIG. 4a shows a third embodiment in a sectional illustration according to FIG. 4, in the case of which the cartridge in the housing of the hand-held device is blocked against being pulled out;

FIG. 5 shows, in longitudinal sectional illustration, the hand-held device in a further embodiment, following separation of an upper housing part from a mouthpiece.

DETAILED DESCRIPTION OF THE INVENTION

Figure 3:
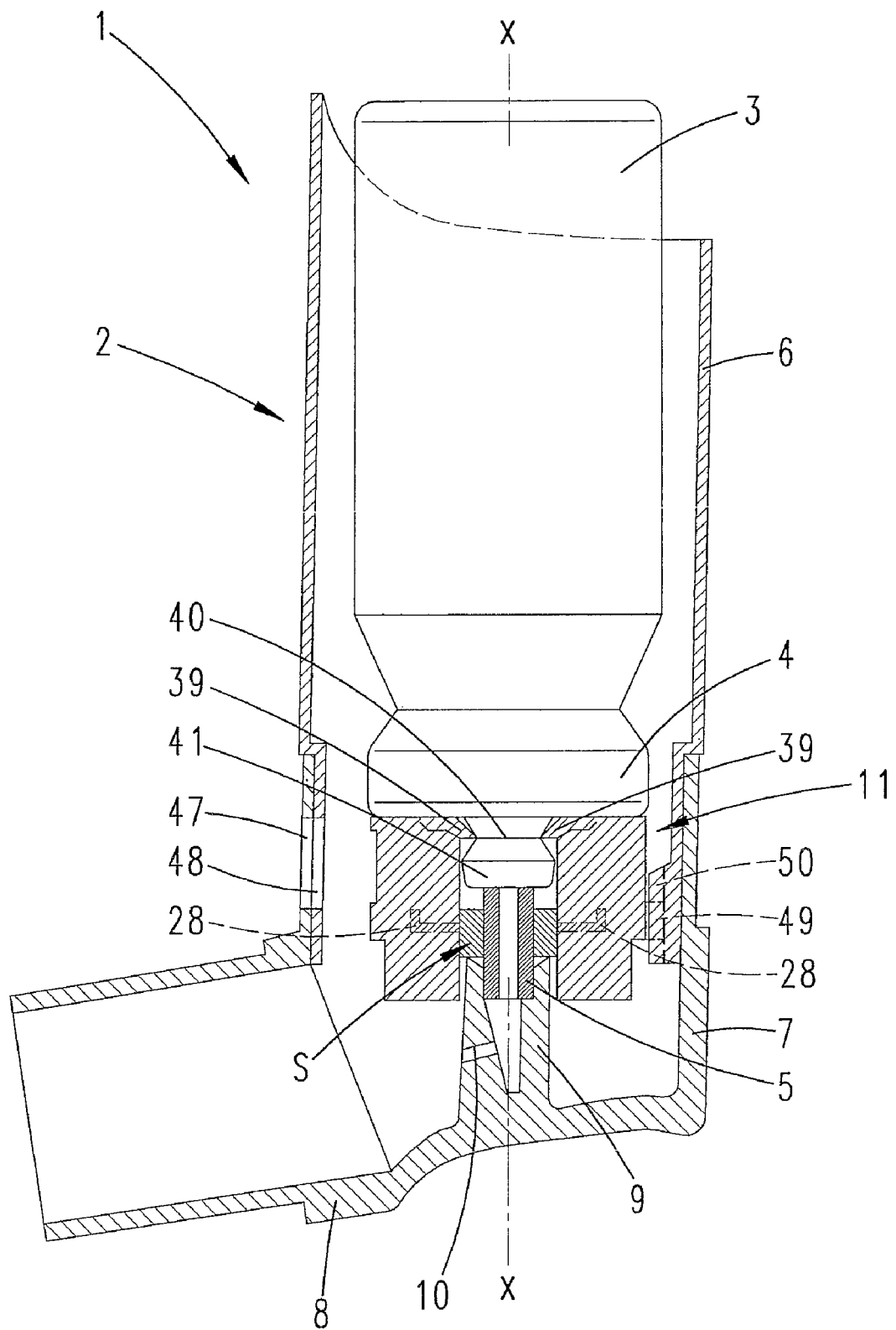
FIG. 3 shows, in longitudinal sectional illustration, the hand-held device in a first embodiment, with a schematically illustrated step-action indexing mechanism latched on a cartridge.

The hand-held unit 1 which is shown in schematic sectional illustration in FIG. 3 serves for apportioned delivery of sprayable substances, in particular inhaler medicaments.

For this purpose, the hand-held unit 1, in first instance, has a hand-held-unit housing 2 into which a cartridge 3 containing the sprayable substance can be inserted. This cartridge 3 is axially displaceable in the housing 2.

In conventional manner, the cartridge head 4 has a central valve tube 5, which extends coaxially in relation to the cartridge 3. A delivery of medicament is achieved via this valve tube by an axial relative movement between the cartridge 3 and housing 2 of the hand-held unit.

The housing 2 of the hand-held device is in two parts and comprises substantially two annular parts 6 and 7 which are disposed one above the other and of which the upper annular part 6 is formed as a passageway and the lower annular part 7 has a mouthpiece 8 oriented approximately transversely to the extent of the passageway. This mouthpiece can be closed by a covering cap (not illustrated).

The valve tube 5 of the cartridge 3 is supported in an associated tubular supporting portion 9 within the lower annular part 7, it being possible for the cartridge 3 to move axially within the passage-form annular part 6, which surrounds the cartridge 3.

The supporting portion 9, which accommodates the valve tube 5 of the cartridge 3 with clamping action and is formed within the lower annular housing part 7, is provided with a flow channel 10 which has a smaller diameter than a portion accommodating the valve-tube end and is connected to the valve tube 5 in terms of flow, that end of the flow channel 10 which is directed away from the valve tube 5 being oriented in the direction of the mouthpiece 8.

The two annular parts 6 and 7 are connected to one another in a plug-in manner in the embodiment illustrated. As an alternative, the two parts may also be connected to one another by a thread, for example a coarse thread with a high pitch.

The arrangement of the cartridge 3 in the housing 2 of the hand-held device is selected so that the head 4 of the cartridge is positioned in the housing 2 approximately at the level of the connecting region between the annular part 6 and the annular part 7.

A step-action indexing mechanism 11 is disposed centrally beneath the opening-side end wall of the cartridge 3, so as to overlap the cartridge valve tube 5. This indexing mechanism serves for registering and indicating the dispensing actuations which have been executed, in dependence on the opening strokes of the cartridge 3 which have been executed.

Figure 1:
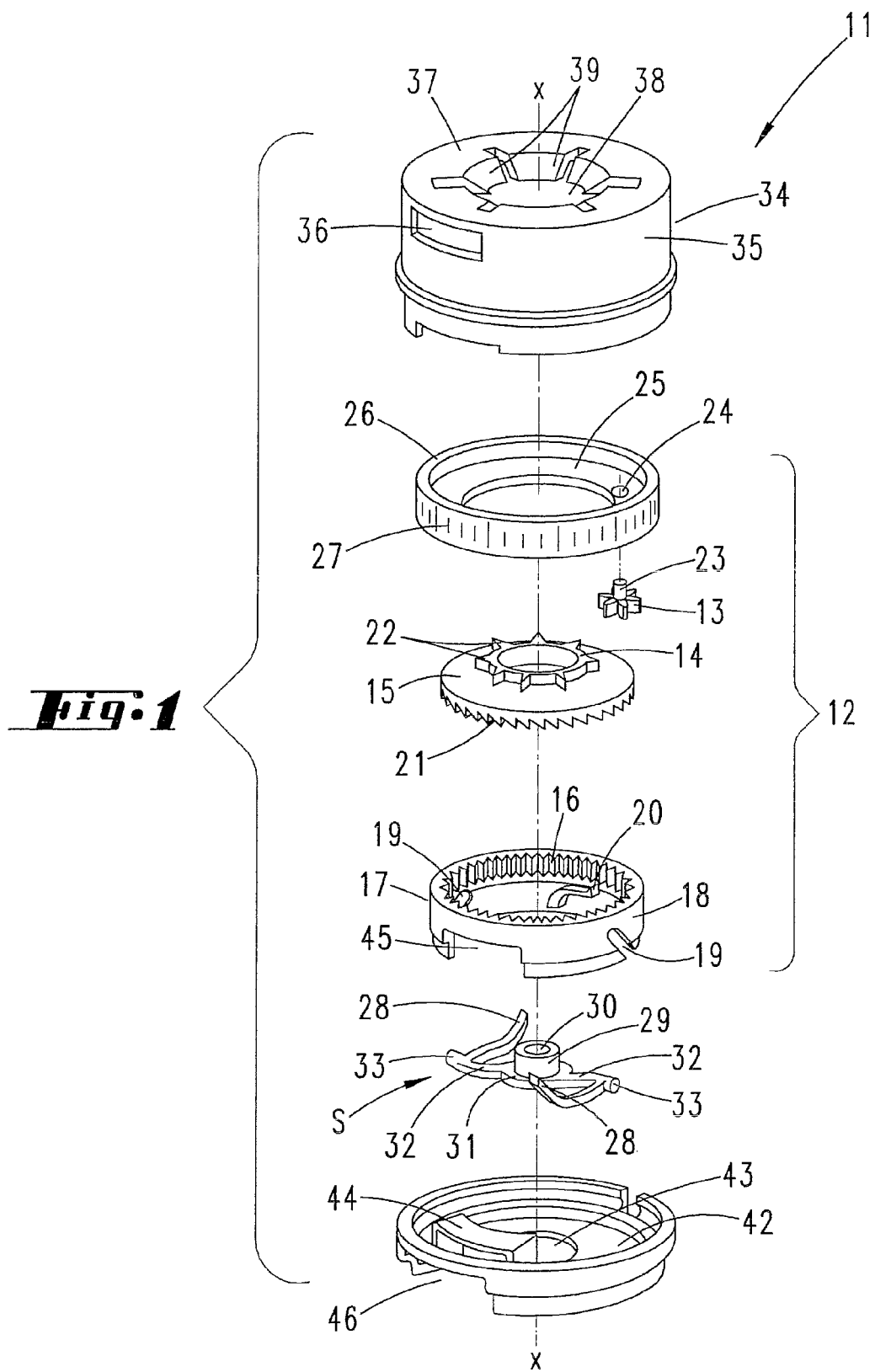
FIG. 1 shows, in exploded perspective illustration, the step-action indexing mechanism for the hand-held device according to the invention.

The step-action indexing mechanism 11 is shown in FIG. 1 in an exploded perspective illustration. The central constituent part of the step-action indexing mechanism 11 is a planet-gear mechanism 12 consisting of a planet gear 13, a sun gear 14, which is seated on a disk 15 which is toothed on the underside, and a toothed rim 16, which interacts with the planet gear 13. This toothed rim is formed on the inner wall of a ring 17 which is in the form of a tube portion and is secured such that it cannot be rotated. The lateral wall 18 of the ring 17 has slots 19 passing through it in diametrically opposite regions, these slots extending, directed obliquely upward, in the indexing direction and opening out downward in the direction of the annular edge which is directed away from the toothed rim 16.

The toothed rim 16 extends axially approximately over half the height of the ring 17, the lateral wall 18 of which, being stepped in the direction of the annular end edge which is directed away from the toothed rim 16, tapers radially.

Beneath the toothed rim 16, a latching finger 20 is integrally formed on the inside of the lateral wall 18 of the ring 17. This latching finger, as seen in a plan view of the ring, is offset radially inward in relation to the toothed rim 16, and accordingly engages in a circular space located radially inside the toothed rim 16. Furthermore, the arrangement of the latching finger 20, which is of elastic formation approximately in the vertical direction, is selected such that this finger engages approximately in a horizontal plane defined by the lower peripheral edges of the toothed rim 16.

The diameter of the disk 15, which carries the sun gear 14, is selected to be slightly smaller than the internal diameter of the ring 17 in the region of the toothed rim 16. The sun gear 14 and disk 15 are preferably formed in one piece, from the same material.

The disk 15 is provided, on its underside, with a sawtooth formation 21 which runs around the periphery and in which the latching finger 20 of the ring 17 engages.

The sun gear 14 has a coarse toothing formation. Thus, in the exemplary embodiment illustrated, eight sun-gear teeth 22 are distributed uniformly over the circumference of the sun gear 14. As the sun gear rotates, these teeth 22 interact with the planet gear 13, which is disposed in the same plane between the sun gear 14 and the toothed rim 16 of the ring 17.

The planet gear 13 has an axial pin 23 which projects upward on one side, i.e. in the direction away from the disk 15 of the sun gear 14. This axial pin is held in a rotatable manner in a bore 24 in the region of a collar 25 of a scale ring 26, this collar being oriented radially inward in a disk-like manner. The scale ring 26 is provided, on its outer lateral wall, with an encircling graduated scale 27, the graduated scale corresponding in each case to a number of individual rotary steps of the planet gear 13, which moves the scale ring forward.

The stepwise displacement of the sun gear 14 and/or of the disk 15, which is integrally formed therewith, takes place via step-action indexing fingers 28 which can yield resiliently approximately in the vertical direction. These fingers engage on the underside of the sawtooth formation 21 of the disk 15.

The step-action indexing fingers 28 are located diametrically opposite one another in relation to the main axis x of the step-action indexing mechanism 11 as a whole. For this purpose, a cylindrical central body in the form of a hub 29 with a central axial through-bore 30 is provided in first instance. The diameter of this through-bore is slightly larger than the external diameter of the cartridge valve tube 5, which is to pass through this through-bore 30.

At the foot end, the hub 29 merges into a radially widened collar 31. Radially projecting guide portions 32 are integrally formed diametrically opposite one another on this collar and, in the region of their free ends in each case, form a guide pin 33, which is positioned in the associated slot 19 of the ring 17.

The step-action indexing fingers 28 each have a horizontal portion rooted on the guide portions 32, leaving the guide pins 33 to project radially outward beyond the horizontal portion. The step-action indexing fingers 28, which project from the horizontal portions, extend directed obliquely upward, with the approximate inclusion of an angle of 45 degrees in relation to the horizontal, this angle being adapted to the slope of the slots 19 in the ring 17. The step-action indexing-finger star thus formed is designated S.

The step-action indexing-finger star S, the ring 17, which contains the inner toothed rim 16, the disk 15, which is integrally formed with the sun gear 14, and the scale ring 26 are aligned concentrically in relation to one another along the axis x, the height of the ring 17 being selected such that both the step-action indexing-finger star S and the sun gear 14, together with the disk 15, are accommodated therein.

The entire planet-gear mechanism 12 as well as the step-action indexing-finger star S and the scale ring 26 are accommodated in a cup-like step-action indexing-mechanism housing 34 with an external diameter adapted to the external diameter of the cartridge 3.

The housing 34 has a lateral wall 35. The latter has a viewing window 36 through which it is possible to see the graduated scale 27 of the scale ring 26.

Figure 2:
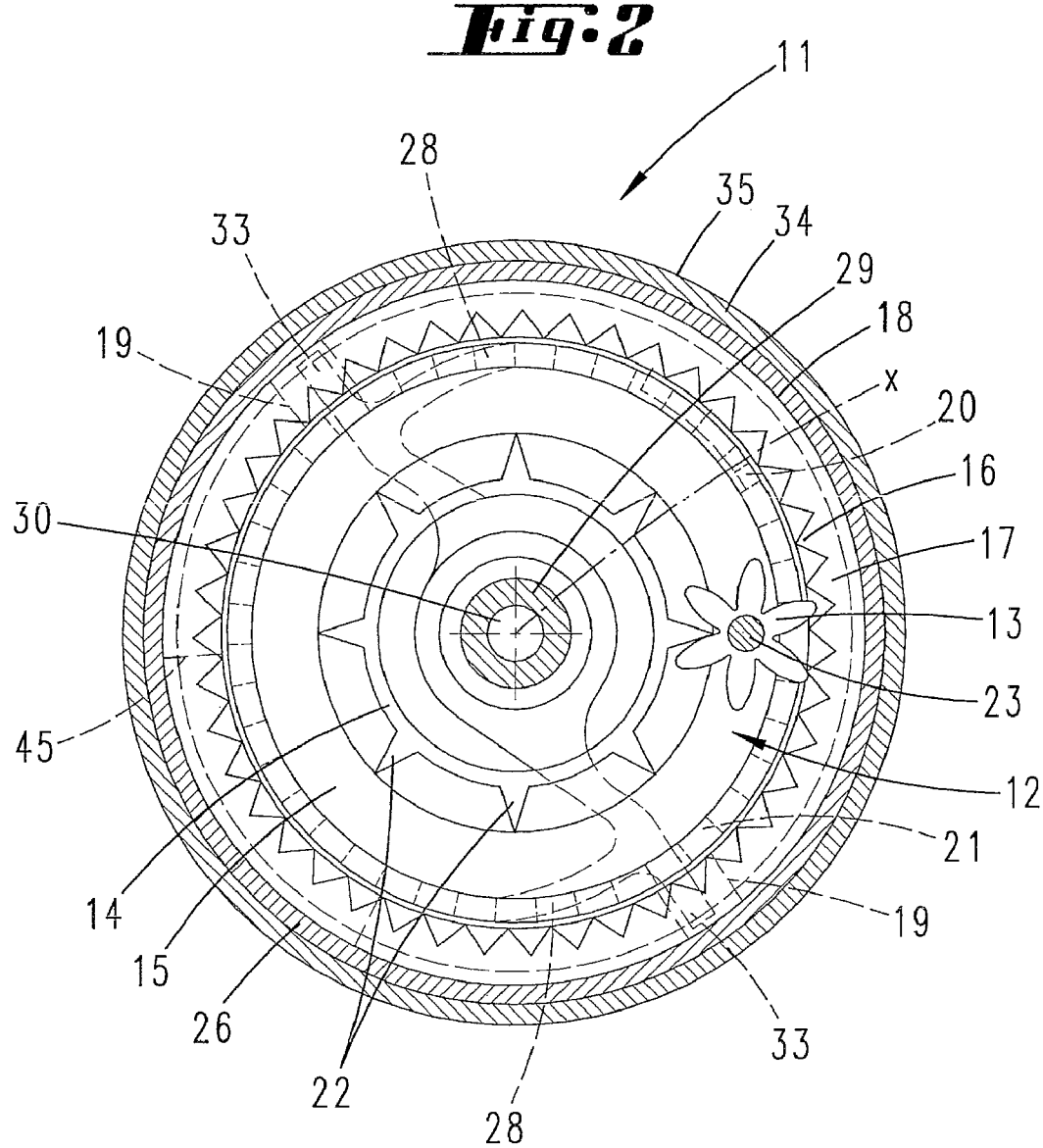
FIG. 2 shows a cross-section through the step-action indexing mechanism.

The housing top 37 has a central aperture 38 which, in the embodiment which is shown in FIGS. 1 to 3, is surrounded by resilient latching tongues 39 which taper conically in the direction of the housing interior in the embodiment 39 shown in FIGS. 1 to 3. The aperture diameter is adapted to a diameter of a waist portion 40 of a collar 41 which projects centrally beyond the opening-side end wall of the cartridge 3 and from which the valve tube 5 extends.

The housing base 42 is formed by a separate part. The latter is connected to the housing 34, for example welded thereto or secured thereon via a press fit, with the above described individual parts of the step-action indexing mechanism being accommodated therein.

The plate-like housing base 42 has a central bore for the valve tube 5 to pass through. Furthermore, the housing base 42 has formed on it a latching component 44 which, for holding the ring 17 in an aligned position, engages in a window-like recess 45 correspondingly formed in the lateral wall 18 of the ring.

Over the same angle region in which the fitting component 44 is disposed on the base, the outer lateral wall of the housing base 42 has a cutout 46. In the installed state, this is associated with the region of the outlet cross-section of the flow channel 10 in the lower annular housing part 7.

Irrespective of the arrangement which is yet to be described basically with reference to FIGS. 3 and 4, the step-action indexing mechanism 11 functions as follows:

The indexing members (step-action indexing-finger star S, ring 17, disk 15, planet gear 13 and scale ring 26), as well as the housing 34 with the housing base 42 are disposed along axes which extend in the longitudinal direction of the cartridge 3. Thus, with the exception of the planet gear 13, all other components of the step-action indexing mechanism 11 are positioned along the longitudinal axis x-x of the cartridge.

The step-action indexing mechanism 11 is accordingly disposed concentrically within the housing 2, within the cross-sectional profile of the cartridge 3, specifically in the installation space left between the cartridge head 4 and supporting portion 9 of the housing 2 of the hand-held device. The step-action indexing mechanism 11 is supported on the end face of the supporting portion 9 of the inhaler housing 2 by way of the hub 29 of the step-action indexing-finger star S, this hub being mounted centrally in the indexing-mechanism housing 34. The central axis x-x of the step-action indexing mechanism 11 is defined by the axis of the body of the cartridge 3. The valve tube 5, which passes through the hub 29, provides for additional centering of the step-action indexing-mechanism unit as a whole.

Upon execution of an actuating stroke of the cartridge 3 and associated vertical displacement of the cartridge in the direction of the supporting portion 9, the indexing-mechanism housing 34 is carried along via the cartridge head 4, this taking place with displacement of the counting-mechanism housing 34, of the planet-gear mechanism 12 and of the scale ring 26 relative to the step-action indexing-finger star S, which is supported on the supporting portion 9. Consequently, the step-action indexing fingers 28, as they are subjected to stressing, and further assisted by the step-action indexing-finger star S sliding upward with rotary action in the lateral-wall slots 19 of the ring 17, cause a stepwise rotary advancement of the sawtoothed disk 15. At the same time, the sun gear 14 rotates by the same angle. The step-action indexing fingers 28 thereby move out of the oblique position in the direction of a plane oriented perpendicularly to the longitudinal axis x-x.

Because the sun gear 14 has merely eight teeth distributed uniformly over the circumference, it is not necessarily the case that every rotary stepping movement of the sun gear 14 results in a rotary movement of the planet gear 13. Rather, the rotation of the planet gear 13 about its axis, and the accompanying rotary displacement of the scale ring 26, takes place only after a number of individual rotary steps of the sun gear 14.

According to the illustration in FIG. 3, the entire step-action indexing mechanism 11 can be secured with latching action, by means of the counting-mechanism housing 34, on the collar 41 that projects from the cartridge head. In association with the viewing window 36 in the housing, the associated portions of the annular housing parts 6 and 7 then likewise have viewing windows 47, 48 which, by virtue of the position selected, directed toward the mouthpiece 8 of the housing 2, are located within the field of vision of the user operating the hand-held unit 1. For introducing the step-action indexing mechanism 11 in a positionally aligned manner, this mechanism is provided with a guide blade 49 which projects radially from the housing 34 and engages in a vertical groove, not illustrated in detail, in the interior of the housing 2 of the hand-held device, allowing the displacement movement during actuation of a stroke.

The latching between the step-action indexing mechanism 11 and the cartridge 3 in the region of the collar 41 at the head of the cartridge is selected so that, when the cartridge 3 is removed from the housing 2, the step-action indexing mechanism 11 is also pulled out, remaining on the cartridge 3 in the process.

Figure 4:
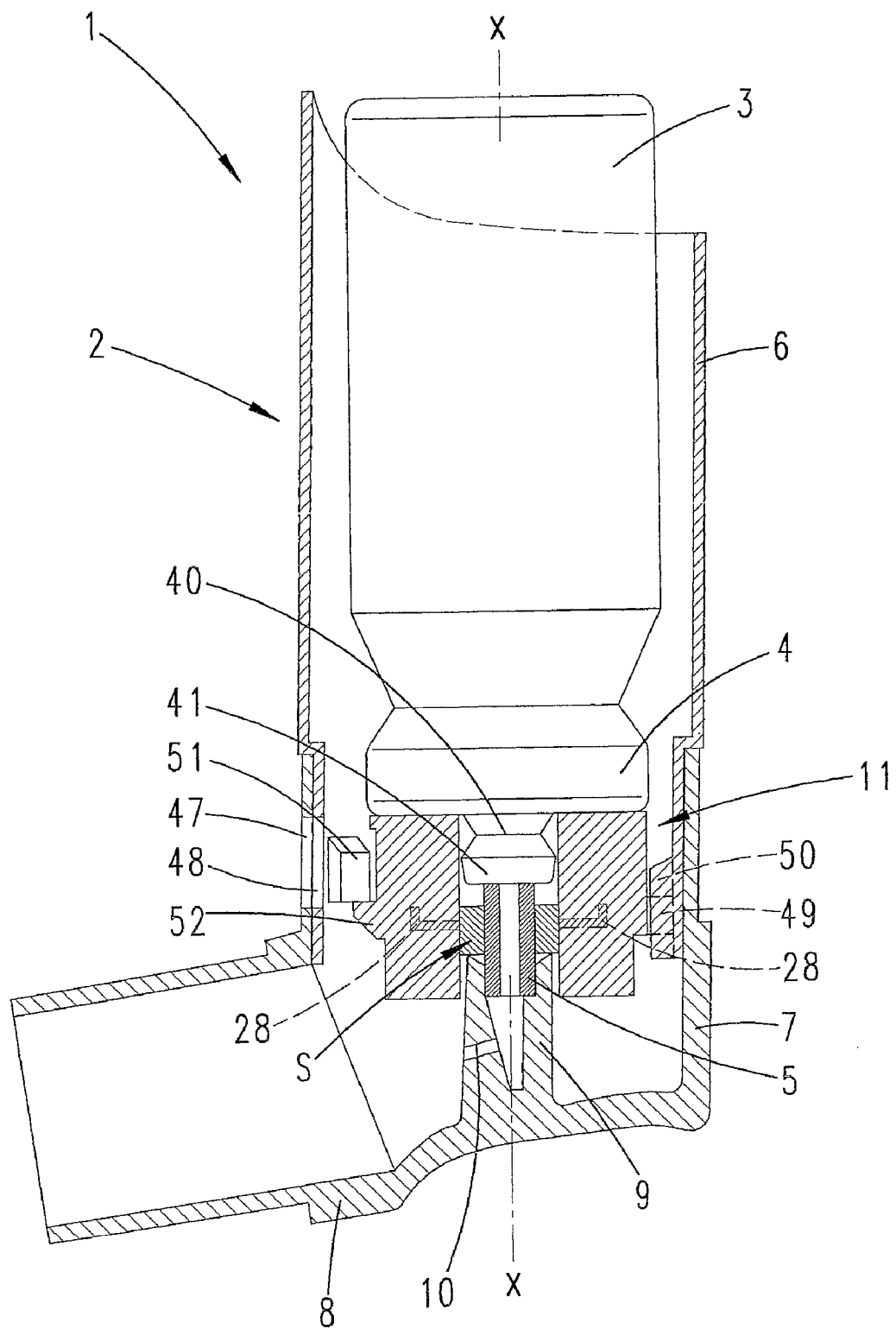
FIG. 4 shows a sectional illustration corresponding to FIG. 3, but relating to a second embodiment, in which the schematically illustrated step-action indexing mechanism is latched on a housing.

As an alternative, it is also possible, as is illustrated schematically in FIG. 4, for the step-action indexing mechanism 11 to be latched to the inhaler housing 2. For this purpose, during initial assembly, the step-action indexing mechanism 11 passes over one or more radially inwardly projecting latching protrusions 51 of the housing 2, following which collar portions 52, that project radially from the indexing-mechanism housing 34, grip beneath these latching protrusions 51.

The latching protrusions 51 are positioned, as seen in the vertical direction, so as to ensure the vertical displaceability of the step-action indexing mechanism 11 upon stroke actuation of the cartridge 3.

The arrangement selected results in the latching protrusions 51 forming holding-down means which keep the step-action indexing mechanism 11 in the housing 2 of the hand-held device when the cartridge 3 is pulled out.

The illustration in FIG. 4a shows a further embodiment, which builds on the configuration which is shown in FIG. 4. Thus, in order to secure the cartridge 3 further—in addition to conventional clamping of the valve tube 5 in the supporting portion 9 in the housing of the hand-held-unit—provision is made for the cartridge 3 to be blocked in the region of the upper annular housing part 6. Obliquely downwardly directed restraining fingers 55 thus project from the inner lateral wall of this upper annular housing part 6 and are formed integrally with the upper housing part 6, from the same material. These restraining fingers 55 are positioned such that their free peripheral edges, positioned in relation to the cartridge 3, pass with blocking action into the waist region of the cartridge 3 which is formed behind the cartridge head 4, in order to thus block the cartridge 3.

Furthermore, the restraining fingers 55 are formed such that, at least when the housing 2 is initially assembled with the cartridge 3, the cartridge head 4 can pass over them.

The cartridge 3 is thus secured to the housing 2 of the hand-held device, in particular at the upper part 6 of the housing.

The illustration in FIG. 5 shows a further embodiment. In this embodiment, the cartridge 3 is also held on the upper housing part 6 by means of restraining fingers 55. This upper housing part 6 can be released from the lower housing part 7, which forms the mouthpiece 8, the two housing parts 6 and 7 being separated approximately in the region where the plate-like step-action indexing-mechanism housing 34 is positioned.

When the two housing parts 6 and 7 have been put together, they are preferably latched, for which purpose one housing part has a latching nose and the other housing part has a correspondingly positioned latching recess.

As a result of this separation being possible, the mouthpiece 8, in particular the angled portion which contains the step portion 9, is easier to clean. This cleaning is further facilitated in that the entire step-action indexing mechanism 11, which is in the form of a compact subassembly, can be removed extremely straightforwardly from the lower housing part 7 and thus brought for separate cleaning. In the exemplary embodiment illustrated, no securing means is provided—such as for example latching protrusions 51 which interact with collar portions 52. Rather, securing of the step-action indexing mechanism 11 as a whole in the lower housing part 7 is effected by interaction with the cartridge 3 in the use position, with the step-action indexing mechanism 11 being aligned between the supporting portion 9 and the facing end face of the cartridge head 4 (as is also illustrated with reference to the embodiment which is shown in FIG. 4a).

It is also the case in this embodiment that the step-action indexing mechanism 11 is secured against rotary displacement about the axis x-x by a positive connection between the step-action indexing mechanism 11 and the lower housing part 7 of the hand-held device.

What is claimed is:

1. A Hand-held device for apportioned delivery of sprayable substances comprising:
   a cartridge which is displaceable by pressing in a housing into an open position for delivery, and
   a step-action indexing mechanism which is actuated by the cartridge during an opening stroke thereof via an annular scale ring that extends circumferentially in front of one or more viewing windows, the step-action indexing mechanism comprising:
   a planet gear, a sun gear and a disk, the sun gear being seated on the disk, the disk being toothed on its underside,
   a ring having a toothed rim formed on its inner wall, the toothed rim interacting with the planet gear, the ring having slots passing through it in diametrically opposite regions, these slots extending, directed obliquely upward, in the indexing direction and opening out downward in the direction of an annular edge which is directed away from the toothed rim,
   a latching finger integrally formed on the inside of the inner wall of the ring, the latching finger being offset radially inward in relation to the toothed rim, and
   a step-action indexing finger star,
   wherein the step-action indexing mechanism and the annular scale ring are disposed in a plate-like indexing mechanism housing, centrally and non-rotatably beneath an opening-side end wall of the cartridge, in overlap with a valve tube of the cartridge, in such a way that the step-action indexing mechanism components and the annular scale ring are located around an axis extending in the longitudinal direction of the cartridge, characterized in that the plate-like indexing mechanism housing together with the enclosed annular scale ring goes down, during actuation, behind the one or more viewing windows of the housing of the hand-held device.

2. The Hand-held device of claim 1, wherein the one or more viewing windows are located on a mouthpiece side of the housing.

3. The Hand-held device of claim 1, further comprising a graduated scale disposed on an outer lateral surface of the annular scale ring and runs in front of a viewing window of the housing, corresponding in each case to a plurality of individual rotary steps of a planet wheel.

4. The Hand-held device of claim 1, wherein the housing of the step-action indexing mechanism is provided in such a manner that, in addition to latching to a collar of the cartridge, a second stronger latching is effected in the housing of the hand-held device.

5. The Hand-held device of claim 1, wherein the device provides for apportioned delivery of inhaler medicaments.

6. The Hand-held device of claim 1, wherein the step-action indexing mechanism is used for registering and displaying delivery actuations which have been carried out.

7. The Hand-held device of claim 1, wherein the housing of the step-action indexing mechanism is cup-like.

* * * * *